United States Patent
Frentzel et al.

(10) Patent No.: US 9,545,460 B2
(45) Date of Patent: *Jan. 17, 2017

(54) PROCESS FOR FRESHENING AIR (71) Applicant: The Procter & Gamble Company, Cincinnati, OH (US)

(72) Inventors: Lisa Grace Frentzel, Cincinnati, OH (US); Robert Richard Dykstra, West Chester, OH (US); Jaden S. Zerhusen, Florence, KY (US); Kathleen Marie Kozak, Fairfield, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 22 days.

This patent is subject to a terminal disclaimer.

(21) Appl. No.: 14/573,436

(22) Filed: Dec. 17, 2014

(65) Prior Publication Data
US 2016/0175470 A1  Jun. 23, 2016

(51) Int. Cl.
| | | |
|---|---|---|
| *C11D 3/50* | (2006.01) | |
| *C11D 3/60* | (2006.01) | |
| *C11D 7/00* | (2006.01) | |
| *A61L 9/02* | (2006.01) | |
| *C11B 9/00* | (2006.01) | |
| *A61L 9/012* | (2006.01) | |

(52) U.S. Cl.
CPC .................. *A61L 9/02* (2013.01); *A61L 9/012* (2013.01); *C11B 9/00* (2013.01)

(58) Field of Classification Search
None
See application file for complete search history.

(56) References Cited

U.S. PATENT DOCUMENTS

| 7,186,680 | B2 * | 3/2007 | Caswell ..................... A47F 1/08 512/4 |
| 7,867,968 | B1 | 1/2011 | Aouad |
| 7,871,976 | B1 * | 1/2011 | Aouad ..................... C08K 7/22 512/2 |
| 2,291,504 | A1 | 4/2011 | Sunder et al. |
| 2,291,505 | A1 | 4/2011 | Wrubbel et al. |
| 8,188,022 | B2 | 5/2012 | Sengupta et al. |
| 2005/0079991 | A1 | 4/2005 | Ranade et al. |
| 2008/0014393 | A1 | 1/2008 | Denome et al. |
| 2008/0305982 | A1 | 12/2008 | Smets et al. |
| 2011/0245143 | A1 * | 10/2011 | Zerhusen ............... C11D 1/645 510/516 |

(Continued)

FOREIGN PATENT DOCUMENTS

| EP | 2 291 504 | B1 | 11/2012 |
| EP | 2 291 505 | B1 | 12/2012 |

OTHER PUBLICATIONS

Notice of Allowance for U.S. Appl. No. 14/573,418, mailed Nov. 24, 2015, 10 pages.
U.S. Appl. No. 14/573,418, filed Dec. 17, 2014, Frentzel et al.

*Primary Examiner* — Peter A Salamon
(74) *Attorney, Agent, or Firm* — Gary J. Foose (57) ABSTRACT

A process for imparting scent to air comprising the steps of: providing a plurality of particles in a reservoir; heating the reservoir to melt the particles to form a melt; and contacting the melt with air; wherein the particles include polyethylene glycol, perfume, and starch granules and each particle has a mass between about 0.95 mg and about 5 grams.

19 Claims, 3 Drawing Sheets (56) References Cited

U.S. PATENT DOCUMENTS

2013/0095717 A1    4/2013    Vanblarcom et al.
2014/0179587 A1*  6/2014    Brown ................ C11D 3/3707
                                                               510/349

* cited by examiner

PROCESS FOR FRESHENING AIR

FIELD OF THE INVENTION

Process for freshening air.

BACKGROUND OF THE INVENTION

There are a variety of technical approaches for providing scent to the air within a household. Potpourri is one approach used to provide such a benefit. Some consumers make their own homemade potpourri mixtures. Other consumers prefer to purchase their potpourri mixtures from retailers.

Scented wax potpourri is commercially available. In practice, the wax is heated to be in a liquid phase and volatile and semi-volatile fragrance components dispersed in the wax are released into the air from the melted wax.

The supply chain for large scale manufacturers of scented wax potpourri to deliver product to the shelves of retailers can be lengthy. This can occur because of the distance between the production facility and the end retailer, which may be on different continents. Further, to limit the risk of not being able to meet retail demand at a particular time, one or more of the manufacturer, distributor, and retailer may maintain inventory that can be tapped to meet and absorb fluctuations in the demand for the product.

As the scented wax composition moves through the supply chain, the product can be exposed to harsh environmental conditions. Potentially detrimental environmental conditions to which the product is exposed include heat and moisture. Commonly, products are shipped via a container on a truck, rail car, or boat. These containers can sit in the sun in hot climates for long durations. Temperatures inside the container can exceed 50° C. and can occur for many days.

The consequence of high temperature in the supply chain can be problematic with respect to the perfume benefits of scented wax potpourri. The degradation of polymeric materials can increase the rate of decomposition of perfume raw materials, resulting in a change in scent intensity of the scented wax potpourri at one or more consumer touch points, such as neat product odor and release of perfume when melted. In addition, some perfume raw materials may be more sensitive than others to degradation, resulting in a change in the character of the scented wax potpourri.

With these limitations in mind, there is a continuing unaddressed need for a process for imparting scent to air employing scented particles that are stable during the length of time between manufacture and use.

SUMMARY OF THE INVENTION

A process for imparting scent to air comprising the steps of: providing a plurality of particles in a reservoir; heating said reservoir to melt said particles to form a melt; and contacting said melt with air; wherein said particles comprise: about 40% to about 95% by weight polyethylene glycol, wherein said polyethylene glycol has a weight average molecular weight from about 5000 to about 11000; about 0.1% to about 20% by weight perfume; and about 0.1% to about 50% by weight starch granules, wherein said starch granules have a dextrose equivalent from 0 to about 40, wherein said starch granules have a grain size of from about 1 µm to about 500 µm, and wherein said starch granules have a starch perfume load level of said perfume on said starch granules of from 0% to about 10% by weight of the starch granules; wherein said particles are substantially homogenously structured particles; and wherein each of said particles has a mass between about 0.95 mg to about 5 grams.

DETAILED DESCRIPTION OF THE INVENTION

The particles of the scented potpourri composition may comprise more than about 40% by weight of the composition of polyethylene glycol. The particles of the scented potpourri composition may comprise about 40% to about 95% by weight of the particles of polyethylene glycol. The polyethylene glycol can have a weight average molecular weight from about 5000 to about 11000. The particles may further comprise from about 0.1% to about 20% by weight of the particles of perfume. The particles may further comprise from about 0.1% to about 50% by weight of the particles of starch granules. The starch granules can have a dextrose equivalent from 0 to about 40. The starch granules can have grain sizes of from about 1 µm to about 500 µm. The starch granules can have a perfume load level of the perfume on the starch granules of from 0% to about 10% by weight of the starch granules. The particles can be substantially homogeneously structured particles. Individually, the particles can have a mass between about 0.95 mg to about 5 grams. The perfume can be encapsulated perfume. The perfume can be unencapsulated perfume.

Polyethylene Glycol (PEG)

Polyethylene glycol (PEG) has a relatively low cost, may be formed into many different shapes and sizes, minimizes unencapsulated perfume diffusion, and melts at a temperature commonly employed in potpourri apparatuses. PEG can be a suitable carrier for other substances delivered in a melt. PEG comes in various weight average molecular weights. A suitable weight average molecular weight range of PEG for the purposes of a scented potpourri composition includes from 2,000 to about 13,000, from about 4,000 to about 12,000, alternatively from about 5,000 to about 11,000, alternatively from about 6,000 to about 10,000, alternatively from about 7,000 to about 9,000, alternatively combinations thereof. PEG is available from BASF, for example PLURIOL E 8000. The PEG can have a weight average molecular weight of 9000.

The particles of the scented potpourri composition can comprise about 40% or more by weight of the particles of PEG. The particles of the scented potpourri composition can comprise about 50% or more by weight of the particles of PEG. The particles of the scented potpourri composition can comprise about 60% or more by weight of the particles of PEG. The particles of the scented potpourri composition of the present invention may comprise from about 65% to about 99% by weight of the particles of PEG. The particles of the scented potpourri composition may comprise about 40% to about 95% by weight of the particles of PEG.

Alternatively, the particles can comprise from about 40% to about 80%, alternatively from about 45% to about 75%, alternatively from about 50% to about 70%, alternatively combinations thereof and any whole percentages or ranges of whole percentages within any of the aforementioned ranges, of PEG by weight of the particles.

The PEG can have a PEG perfume load level. The PEG perfume load level is the ratio of the mass of perfume in the PEG to the mass of PEG. To promote release of perfume, it can be desirable for the PEG perfume load level to be greater than the starch perfume load level discussed herein. The PEG perfume load level can be measured and compared to the starch perfume load level by 1) heating a sample of the scented potpourri composition containing PEG, perfume and starch granules above its melting point, 2) centrifuging the sample to separate the molten (liquid) PEG phase from the starch granules phase, 3) removing an equal weight portion of both phases, 4) diluting each phase with suitable level of methanol to enable measuring of the relative perfume levels of each phase via standard gas chromatograph and mass spectrometer techniques.

Balancing Agent

The particles of the scented potpourri composition described herein can comprise from about 0.1% to about 10% by weight of the particles of a balancing agent selected from the group consisting of glycerin, polypropylene glycol, isopropyl myristate, dipropylene glycol, 1,2 propanediol, PEG having a weight average molecular weight less than 2,000, and mixtures thereof. The balancing agent can be dipropylene glycol. As used herein, PEG having a weight average molecular weight less than 2,000 is a balancing agent. So, the balancing agent can be PEG having a weight average molecular weight less than 2000. PEG having a weight average molecular weight from 2,000 to about 13,000 is not a balancing agent. PEG having a weight average molecular weight from 2,000 to about 13,000 can be a major component of the particles.

The balancing agent for any of the particles disclosed herein can be selected from the group consisting of isopropyl myristate, dipropylene glycol, and mixtures thereof. Isopropyl myristate can be a suitable balancing agent at a level of about 4% by weight of the particles. Isopropyl myristate can be provided with the unencapsulated perfume.

The balancing agent can be polypropylene glycol. The balancing agent can be polypropylene glycol can have weight average molecular weight less than about 400, alternatively less than about 1,000, alternatively less than about 2,000, alternatively less than about 4,000.

It has been found that levels of PEG having a weight average molecular weight from about 2,000 to about 13,000 forming less than about 98% by weight of the particles can be desirable to provide for uniform formation of particles of a consumer desirable size via a rotoforming process. Optionally, the level of such PEG can be less than about 95% by weight of the particles, less than about 91% by weight of the particles, less than about 88% by weight of the particles, or less than about 80% by weight of the particles. Using a lower fraction of PEG can be desirable to reduce cost and to provide formula space for the inclusion of starch granules.

Some unencapsulated perfumes have such intense scents that they can be overwhelming to consumers. Thus, for intense unencapsulated perfumes, only a limited mass fraction of one or more of those components is needed to deliver the desired scent experience. In view that the desirable level of PEG can be less than about 91% by weight of the particles, if only a limited mass fraction of the unencapsulated perfume is used, it may not be possible to produce particles having the desired size and shape, unless a balancing agent is provided in the composition. If an array of scented potpourri compositions is to be provided, the inability to provide for uniformity amongst the particles in the different scent variants across the array can be disconcerting to the consumer. Consumers tend to expect that the products of a single brand within a single category of goods will each have a similar look and feel as well as a similar function and efficacy.

The balancing agent should not interfere with the performance of the particles of the composition, for example by significantly altering the scent, color, or the melting of the particles. Further the balancing agent should have a suitably small effect on the melting point of the composition so that a variety of compositions having different scent can be manufactured within a narrow range or even the same range of process settings. Balancing agents selected from the group consisting of glycerin, polypropylene glycol, isopropyl myristate, dipropylene glycol, 1,2 propanediol, PEG having a weight average molecular weight less than 2,000, and mixtures thereof are thought to not interfere with production of and performance of the particles of the composition. Since the balancing agent is offsetting having to include additional PEG to form particles having the desired size and shape, the balancing agent is desirably less expensive or at least cost-competitive with PEG, compatible with the process used to form the particles, easy to employ in the process used to form the particles, and readily available for supply in commercially viable quantities.

The balancing agent can also be practical in that it can allow the formulation of an array of scented potpourri compositions comprising particles that have similar, if not essentially the same, size, shape, and production characteristics and having a relatively narrow range of PEG levels. Having a narrow range of PEG levels can allow the manufacturer to use a single set of processing conditions to produce particles having different levels of unencapsulated perfume, with the balance of the formula comprising the balancing agent, accounting for the inclusion of any dyes and/or formula minors.

For example, consider a first scented potpourri composition and a second scented potpourri composition, the particles of the first scented potpourri composition having a first unencapsulated perfume and the particles of the second scented potpourri composition having a second unencapsulated perfume. If the intensity of the first unencapsulated perfume is greater than the intensity of the second unencapsulated perfume, to have similar scent intensity of the unencapsulated perfume in the particles across the array of scented potpourri compositions, a lower level of first encapsulated can be offset with the balancing agent. This will allow the PEG levels for the particles of the two compositions to be within a narrow range so that the same manufacturing conditions can be used to produce the particles of both, or more, compositions.

The particles of the scented potpourri compositions described herein can comprise from about 0.5% to about 5% by weight of the particles of a balancing agent selected from the group consisting of glycerin, polypropylene glycol, isopropyl myristate, dipropylene glycol, 1,2 propanediol, PEG having a weight average molecular weight less than 2,000, and mixtures thereof. The balancing agent for any of the compositions disclosed herein can be dipropylene glycol. The balancing agent for any of the compositions disclosed herein can be isopropyl myristate.

Perfume

The particles of the scented potpourri composition of the present invention may comprise an unencapsulated perfume and/or optionally perfume microcapsules. Perfumes are generally described in U.S. Pat. No. 7,186,680 at column 10, line 56, to column 25, line 22. The particles of the scented potpourri composition can comprise unencapsulated perfume and can be essentially free of perfume carriers, such as a perfume microcapsule. Optionally, the particles of the scented potpourri composition can comprise perfume carrier materials (and perfume contained therein). Examples of perfume carrier materials are described in U.S. Pat. No. 7,186,680, column 25, line 23, to column 31, line 7. Specific examples of perfume carrier materials may include cyclodextrin and zeolites.

For the compositions disclosed herein, it is not necessary that the particles of the scented potpourri composition comprise unencapsulated perfume at the time of manufacture. Rather, unencapsulated perfume at the time of manufacture can be an optional component. The starch can provide for perfume stability of unencapsulated perfume provided in the particle at the time of manufacture and unencapsulated perfume in the particle that might exist as a result of leakage from perfume microcapsules that are provided at the time of manufacture. Unencapsulated perfume can be desirable to provide scent to the particles so that the user of the particles experiences a pleasant smell when she dispenses the particles or opens a container containing the particles.

The particles can comprise about 0.1% to about 20%, alternatively about 1% to about 15%, alternatively 2% to about 10%, alternatively combinations thereof and any whole percentages within any of the aforementioned ranges, of perfume by weight of the particles of the scented potpourri composition. The perfume can be unencapsulated perfume and or optionally encapsulated perfume.

The particles of the scented potpourri composition can comprise unencapsulated perfume and be free or essentially free of a perfume carrier. The particles of the scented potpourri composition may comprise about 0.1% to about 20%, alternatively about 1% to about 15%, alternatively 2% to about 10%, alternatively combinations thereof and any whole percentages within any of the aforementioned ranges, of unencapsulated perfume by weight of the particles of the scented potpourri composition.

The particles can comprise unencapsulated perfume and optionally perfume microcapsules. The particles may comprise about 0.1% to about 20%, alternatively about 1% to about 15%, alternatively from about 2% to about 10%, alternatively combinations thereof and any whole percentages or ranges of whole percentages within any of the aforementioned ranges, of the unencapsulated perfume by weight of the particles. Such levels of unencapsulated perfume can be appropriate for any of the particles disclosed herein that have unencapsulated perfume.

The particles can comprise unencapsulated perfume and optionally perfume microcapsules but be free or essentially free of other perfume carriers. The particles can comprise unencapsulated perfume and perfume microcapsules and be free of other perfume carriers.

The particles of the scented potpourri compositions of the present invention can optionally comprise encapsulated perfume. Encapsulated perfume can be provided as plurality of perfume microcapsules. A perfume microcapsule is perfume oil enclosed within a shell. The shell can have an average shell thickness less than the maximum dimension of the perfume core. The perfume microcapsules can be friable perfume microcapsules. The perfume microcapsules, if present, can be moisture activated perfume microcapsules.

The perfume microcapsules can comprise a melamine/formaldehyde shell. Perfume microcapsules may be obtained from Appleton, Quest International, or International Flavor & Fragrances, or other suitable source. The perfume microcapsules can be those described in U.S. Patent Pub. 2008/0305982.

The particles optionally can comprise about 0.1% to about 20%, alternatively about 1% to about 15%, alternatively about 2% to about 10%, alternatively combinations thereof and any whole percentages within any of the aforementioned ranges, of encapsulated perfume by weight of the particles of the scented potpourri composition.

The particles can optionally comprise perfume microcapsules but be free of or essentially free of unencapsulated perfume. The particles may comprise about 0.1% to about 20%, alternatively about 1% to about 15%, alternatively about 2% to about 10%, alternatively combinations thereof and any whole percentages within any of the aforementioned ranges, of encapsulated perfume by weight of the particles of the scented potpourri composition.

Starch Granules

The particles of the scented potpourri composition can comprise from about 0.1% to about 50% by weight of the particles of starch granules. Including starch granules in the particles can provide for improved perfume stability from the time of manufacture to the time of purchase as compared to particles that do not include starch granules. The particles of the scented potpourri composition can comprise from about 0.1% to about 40% by weight of the particles of starch granules. The particles of the scented potpourri composition can comprise from about 0.1% to about 30% by weight of the particles of starch granules. The starch granules can be MELOJEL corn starch from Ingredion. The starch granules can be wheat, rice, potato, tapioca. The starch granules can be a polysaccharide material such as cellulose, xanthan gum, or gum arabic.

Starch is a polysaccharide consisting of a large number of glucose units joined by a glycosidic bond. It is produced by most green plants and can be found in large amounts in staple foods such as corn, wheat, rice and potatoes. One example is unmodified corn starch, such as Melojel corn starch from Ingredion.

The starch granules can have a dextrose equivalent from 0 to about 40. Dextrose equivalent is a characterization of the degree of hydrolyzation of the starch into simpler carbohydrates. The extent of conversion of starch is quantified by dextrose equivalent, which is roughly the fraction of glucosidic bonds that have been broken, or the degree of starch polymer hydrolysis, which is controlled by the hydrolysis reaction. It is a measure of reducing power, in the form of reducing sugars, compared to a dextrose standard of 100. The higher the dextrose equivalent, the greater the extent of starch hydrolysis. Fully hydrolyzed starch, or dextrose, has a dextrose equivalent of 100. Unmodified starch has a dextrose equivalent of 0. Maltodextrins are made by partial hydrolysis of corn starch with suitable acids and/or enzymes and have a dextrose equivalent of less than 20. Corn syrup solids and liquid corn syrups have a dextrose equivalent of greater than 20. The starch granules can have a dextrose equivalent from 0 to about 25.

Starch granules and granules of starch derivatives having a dextrose equivalent from 0 to about 40 are thought to be able to provide a perfume stability benefit and are easily formulated into the particles of the scented potpourri composition. More particularly, starch granules and granular starch derivatives having a dextrose equivalent from 0 to about 25 can provide a perfume stability benefit. Such starch granules are thought to be easily formulated into the particles of the scented potpourri composition. Starch granules having a dextrose equivalent of about 0 can be practical. The benefits of such starch granules are thought to include less negative environmental impact, they may be easier to process in a melt as they may not thicken the melt as much, may be readily available in particles sizes within a desirable range, and may not swell as much as hydrolyzed starch granules. MELOJEL available from INGREDION, Bridgewater, N.J., United States of America can be practical.

Granular starch derivatives having a dextrose equivalent between about 25 and about 40 may be more difficult to employ in formulations. Without being bound by theory, it is thought that higher dextrose equivalent starch granules can form particle networks that can lead to unwanted gelling or viscosity growth in the PEG hot melt. Higher dextrose equivalent may also reduce the desired improvement in perfume stability. Without being bound by theory, it is thought that increased starch hydrolysis and higher dextrose equivalent leads to materials that are less capable of slowing unwanted autoxidation reactions as compared to starch granules having lower hydrolysis and lower dextrose equivalent.

The dextrose equivalent of the starch granules is measured using the method of ISO 5377:1981.

To evaluate the ability to process melts into particles, melts having different starch components were prepared. The melts were formed of 67.17% by weight PEG having a weight average molecular weight of 8000, 1.08% by weight dipropylene glycol, 7.50% by weight unencapsulated perfume, 4.04% by weight perfume microcapsules (1.13% by weight active perfume microcapsules), 0.20% by weight dye (5% by weight active), 20.00% by weight starch material as set forth in Table 1, and 0.01% by weight butylated hydroxytoluene. The perfume microcapsules would be an optional component of the formulation and might be beneficial if the particles have the capability to be used as both a fabric treatment composition and scented potpourri composition.

To make the melts, molten PEG was loaded into a mixing vessel having temperature control to keep the batch materials at about 80° C. during mixing. The individual remaining components of the mixture were mixed into the PEG serially with the mixture being observed to be homogeneous prior to introducing an additional component to the melt.

An attempt was made to spread the mixture into molds having a hemispherical shape having a diameter of about 5 mm and a height of about 2.5 mm. After cooling and hardening of melts that could be formed into the molds, the resulting particles were removed from the mold. The character of processing for each such melt prepared is summarized in Table 1 with the character of processing being descriptive of whether particles could be formed or not.

TABLE 1

Character of processing of a melt consisting of 67.17% by weight PEG having a weight average molecular weight of 8000, 1.08% by weight dipropylene glycol, 7.50% by weight unencapsulated perfume, 4.04% by weight perfume microcapsules, 0.20% by weight dye (5% by weight active), 20.00% by weight starch material, and 0.01% by weight butylated hydroxytoluene.

| Starch Material | Character of Processing |
|---|---|
| Dextrose Equivalent = 0 (solid) | |
| Corn starch (MELOJEL) | Able to produce particles |
| Dextrose Equivalent 1-25 (solid) | |
| Maltodextrin (STAR DRI 1) | Able to produce particles |
| Maltodextrin (STAR DRI 10) | Able to produce particles |
| Maltodextrin (Maltrin M180) | Able to produce particles |
| Maltodextrin (Maltrin M250) | Able to produce particles |

TABLE 1-continued

Character of processing of a melt consisting of 67.17% by weight PEG having a weight average molecular weight of 8000, 1.08% by weight dipropylene glycol, 7.50% by weight unencapsulated perfume, 4.04% by weight perfume microcapsules, 0.20% by weight dye (5% by weight active), 20.00% by weight starch material, and 0.01% by weight butylated hydroxytoluene.

| Starch Material | Character of Processing |
|---|---|
| Dextrose Equivalent = 42 (solid) | |
| Corn Syrup (STAR DRI 42) | Unable to produce particles |
| Dextrose Equivalent 26-63 (liquid) | |
| Corn Syrup (Staley 200) | Unable to produce particles |
| Corn Syrup (Staley 1300) | Unable to produce particles |
| Corn Syrup (NETO 7350) | Unable to produce particles |
| Corn Syrup (SWEETOSE 4425) | Able to produce particles |
| Dextrose Equivalent 100 (solid) | |
| Dextrose | Able to produce particles |

To further evaluate the ability to process melts into particles, melts having a starch weight percentage of 10.00% were prepared. Melts were formed of 77.24% by weight PEG having a weight average molecular weight of 8000, 8.20% by weight unencapsulated perfume, 4.41% by weight perfume microcapsules, 0.14% by weight dye (5% by weight active), 0.01% by weight butylated hydroxytoluene, and 10.00% by weight starch material as set forth in Table 2. The character of processing for each such melt prepared is summarized in Table 2. The perfume microcapsules would be an optional component of the formulation and might be beneficial if the particles have the capability to be used as both a fabric treatment composition and scented potpourri composition.

TABLE 2

Character of processing of a melt consisting of 77.24% by weight PEG having a weight average molecular weight of 8000, 8.20% by weight unencapsulated perfume, 4.41% by weight perfume microcapsules, 0.14% by weight dye (5% by weight active), 0.01% by weight butylated hydroxytoluene, and 10.00% by weight starch material.

| Starch Material | Character of Processing |
|---|---|
| Dextrose Equivalent = 0 (solid) | |
| Corn starch (MELOJEL) | Able to produce particles |
| Dextrose Equivalent 1-25 (solid) | |
| Maltodextrin (Maltrin M180) | Able to produce particles |

For both the 10% by weight starch granules and the 20% by weight starch material, particles we able to be formed when the starch had a dextrose equivalents between 0 and 25.

To evaluate the improvement in perfume stability obtained by including starch granules in the particles, two formulations were compared. The control formula was 87.36% by weight PEG having a weight average molecular weight of 8000, 0.01% by weight butylated hydroxytoluene, 0.85% by weight dipropylene glycol, 7.50% by weight unencapsulated perfume, 4.04% by weight perfume microcapsules, and 0.24% by weight dye (5% by weight active). The test formula was 65.52% by weight PEG having a weight average molecular weight of 8000, 0.01% by weight butylated hydroxytoluene, 0.85% by weight dipropylene glycol, 7.50% by weight unencapsulated perfume, 4.04% by weight perfume microcapsules, 0.24% by weight dye (5% by weight active), and 21.84% by weight starch granules. The perfume microcapsules would be an optional component of the formulation and might be beneficial if the particles have the capability to be used as both a fabric treatment composition and scented potpourri composition.

The particles were formed in the same manner as that described previously with respect to evaluating the character of processing melts. After forming particles, specimens of each formulation were stored at 35° C. for one year. Perfume was extracted from the control formula without starch and the test formula having starch and the mass of the perfume raw materials was measured using gas chromatography and mass spectrometry. The results reported in Table 3 are normalized against the mass of the respective perfume raw material in the control formula after storage. So, for example, the mass of octanal in the formula having starch granules was 2.1 times greater than the mass of octanal in the formula without starch granules.

TABLE 3

Normalized mass of perfume raw materials in particles after 1 year of storage.

| Perfume Raw Material | Control Formula (No Starch Granules) | Test Formula (21.84% by Weight Starch Granules) |
| --- | --- | --- |
| Octanal | 1.0 | 2.1 |
| Ligustral | 1.0 | 3.7 |
| Nonanal | 1.0 | 2.5 |
| Decanal | 1.0 | 2.7 |
| Iso-eugenol | 1.0 | 9.0 |
| Methyl nonyl acetaldehyde | 1.0 | 14.3 |
| Lilial | 1.0 | 20.2 |
| Sanjinol | 1.0 | 2.4 |
| Dihydromyrcenol | 1.0 | 0.9 |
| Verdox | 1.0 | 0.9 |
| Undecalactone | 1.0 | 1.0 |

Without being bound by theory, it is thought that including starch in the particles improves perfume stability during storage. As shown in Table 3, after one year of storage, particles having starch granules tend to have a greater mass of most of the listed perfume raw materials than particles that do not have starch granules.

The starch granules can have a grain size between about 1 µm and about 500 µm. The starch granules can have a grain size between about 1 µm and about 200 µm. The starch granules can have a grain size between about 1 µm and about 30 µm. Without being bound by theory, it is thought that smaller grain sizes of starch granules are associated with improved stability of the perfume in the particles.

The starch granules can have a starch perfume load level of from 0% to about 10% by weight of the starch granules. The starch perfume load level is the ratio of the mass of perfume absorbed to the starch granules to the mass of the starch granules. The starch granules can have a starch perfume load level of from 0% to about 5% by weight of the starch granules. The starch granules can have a starch perfume load level of from 0% to about 2% by weight of the starch granules. The starch granules can have a starch perfume load level of from 0% to about 1% by weight of the starch granules. Prior to manufacture of the composition, the starch granules can be substantially free or free from unencapsulated perfume. A starch that is not hydrophobically or cationically modified or modified with moieties that significantly improve the ability of the starch to self-emulsify perfume can be practical.

The PEG perfume load level can be measured and compared to the starch perfume load level by 1) heating a sample of the scented potpourri composition containing PEG, perfume and starch granules above its melting point, 2) centrifuging the sample to separate the molten (liquid) PEG phase from the starch phase, 3) removing an equal weight portion of both phases, 4) diluting each phase with suitable level of methanol to enable measuring of the relative perfume levels of each phase via standard gas chromatograph and mass spectrometer techniques.

The PEG perfume load level can be greater than the starch perfume load level. The PEG perfume load level can be more than about 1.3 times the starch perfume load level. The PEG perfume load level can be more than about 2 times the starch perfume load level. The PEG perfume load level can be more than about 4 times the starch perfume load level. The PEG perfume load level can be more than about 6 times the starch perfume load level. The PEG perfume load level can be more than about 10 times the starch perfume load level. Higher ratios of the PEG perfume load level to the starch perfume load level are thought to provide for improved release of the perfume contained in the particles.

By maintaining a relatively low level of perfume loading on the starch granules, the perfume provided in the particles can be more freely available for the consumer to experience. Starch can have a tendency to restrain from release perfumes that are typically used in scented potpourri applications. Thus, having a limited amount of perfume fixed with the starch granules can be desirable to promote perfume bloom and provide for scent of the particles at the point of purchase.

Dye

The particles may comprise dye. The dye may include those dyes that are typically used in scented potpourri compositions. The scented potpourri composition may comprises less than about 0.1%, alternatively about 0.001% to about 0.1%, alternatively about 0.01% to about 0.02%, alternatively combinations thereof and any hundredths of percent or ranges of hundredths of percent within any of the aforementioned ranges, of dye by weight of the particles of scented potpourri composition. Examples of suitable dyes include, but are not limited to, LIQUITINT PINK AM, AQUA AS CYAN 15, and VIOLET FL, available from Milliken Chemical. Employing a dye can be practical to help the user differentiate between particles having differing scents.

Particles

Particles may be formed by processes including those disclosed in U.S. Pat. Nos. 5,013,498 and 5,770,235. Particles can be practically formed by processing a melt of the composition that subsequently forms the particles. The melt of the particles of the present invention may be prepared in either batch or continuous mode. In batch mode, molten PEG is loaded into a mixing vessel having temperature control. Starch granules, if present, can then be added and mixed with PEG until the mixture is substantially homogeneous. Balancing agent, if present, can then be added and mixed until the mixture is substantially homogeneous. Perfume can be added to the PEG. The mixture can be mixed until the mixture is substantially homogeneous. Encapsulated perfume, if present, can be added and mixed until the mixture is substantially homogeneous. Dye, if present, can then be added to the vessel and the components are further mixed for a period of time until the entire mixture is substantially homogeneous. In continuous mode, molten PEG is mixed with starch granules, if present, unencapsulated perfume, if present, and perfume microcapsules, if present, in an in-line mixer such as a static mixer or a high shear mixer and the resulting substantially homogeneous mixture is then used to make the particles. Balancing agent, if present, perfume microcapsules, if present, and unencapsulated perfume, if present, can be added to PEG in any order or simultaneously and dye can be added at a step prior to making the particles or any other suitable time.

The particles can be made according to the following process. Molten PEG can be provided. Starch granules can be premixed with the PEG prior to forming the melt, for example to simplify material handling and or minimize the number of tanks required to manufacture the particles. Starch granules can be mixed with the PEG. Perfume can be mixed with the PEG. Together, the molten PEG, starch granules, and perfume can form a melt. The melt can be formed into particles. Optionally, perfume microcapsules can be mixed with the PEG. The particles can be formed by passing the melt through small openings. The particles can be formed by depositing the melt in a mold. The particles can be formed by spraying the melt onto a chilled surface. The chilled surface can be a chilled drum. The chilled drum can be a rotating chilled drum.

The particles may be formed into different shapes including tablets, pills, spheres, and the like. A particle can have a shape selected from the group consisting of spherical, hemispherical, compressed hemispherical, lentil shaped, and oblong. Lentil shaped refers to the shape of a lentil bean. Compressed hemispherical refers to a shape corresponding to a hemisphere that is at least partially flattened such that the curvature of the curved surface is less, on average, than the curvature of a hemisphere having the same radius. A compressed hemispherical particle can have a ratio of height to diameter of from about 0.01 to about 0.4, alternatively from about 0.1 to about 0.4, alternatively from about 0.2 to about 0.3. Oblong shaped refers to a shape having a maximum dimension and a maximum secondary dimension orthogonal to the maximum dimension, wherein the ratio of maximum dimension to the maximum secondary dimension is greater than about 1.2. An oblong shape can have a ratio of maximum dimension to maximum secondary dimension greater than about 1.5. An oblong shape can have a ratio of maximum dimension to maximum secondary dimension greater than about 2. Oblong shaped particles can have a maximum dimension from about 2 mm to about 15 mm and a maximum secondary dimension of from about 2 mm to about 10 mm. Oblong shaped particles can have a maximum dimension from about 2 mm to about 10 mm and a maximum secondary dimension of from about 2 mm to about 7 mm. Oblong shaped particles can have a maximum dimension from about 2 mm to about 6 mm and a maximum secondary dimension of from about 2 mm to about 4 mm.

Particles 30 having an oblong shape can be indicative of suitable particle making conditions. For particles 30 produced from a melt, an oblong shape can be an indication that suitable processing conditions are being employed with respect to one or more of temperature of the melt, conveyor surface speed, conveyor surface temperature, or other process condition. When a melt from which particles 30 are prepared is at a sufficiently high temperature, the melt will tend to flow and a surface of the yet to be formed particle 30 will spread out in the machine direction of the conveyor surface after the melt is deposited on the conveyor surface. If the temperature of the melt is too low, forming substantially uniformly shaped particles 30 can be challenging.

Optionally, for any of the formulations disclosed herein, individual particles 30 can have a mass from about 0.95 mg to about 5 g, alternatively from about 0.95 mg to about 2 g, alternatively from about 10 mg to about 1 g, alternatively from about 10 mg to about 500 mg, alternatively from about 10 mg to about 250 mg, alternatively from about 0.95 mg to about 125 mg, alternatively combinations thereof and any whole numbers or ranges of whole numbers of mg within any of the aforementioned ranges. In a plurality of particles 30, individual particles 30 can have a shape selected from the group consisting of spherical, hemispherical, compressed hemispherical, lentil shaped, and oblong.

An individual particle 30 may have a volume from about 0.003 cm$^3$ to about 5 cm$^3$. An individual particle 30 may have a volume from about 0.003 cm$^3$ to about 1 cm$^3$. An individual particle 30 may have a volume from about 0.003 cm$^3$ to about 0.5 cm$^3$. An individual particle 30 may have a volume from about 0.003 cm$^3$ to about 0.2 cm$^3$. An individual particle 30 may have a volume from about 0.003 cm$^3$ to about 0.15 cm$^3$. Smaller particles 30 are thought to provide for better packing of the particles 30 in a container and faster melting of the particles 30 in a potpourri apparatus.

The composition can comprise particles 30 that are retained on a number 10 sieve as specified by ASTM International, ASTM E11-13. The composition can comprise particles 30 wherein more than about 50% by weight of the particles 30 are retained on a number 10 sieve as specified by ASTM International, ASTM E11-13. The composition can comprise particles 30 wherein more than about 70% by weight of the particles 30 are retained on a number 10 sieve as specified by ASTM International, ASTM E11-13. The composition can comprise particles 30 wherein more than about 90% by weight of the particles 30 are retained on a number 10 sieve as specified by ASTM International, ASTM E11-13. It can be desirable to provide particles 30 sized as such because particles retained on a number 10 sieve me be easier to handle than smaller particles.

Without being bound by theory the inclusion of starch in the particles 30 can reduce perfume degradation in the particles 30 associated with autoxidation of the perfume carried in the particles 30. Without being bound by theory, it is thought that the benefit associated with including starch increases with decreasing size of the particles 30.

The composition can comprise particles 30 that pass a sieve having a nominal sieve opening size of 22.6 mm. The composition can comprise particles 30 that pass a sieve having a nominal sieve opening size of 22.6 mm and are retained on a sieve having a nominal sieve opening size of 0.841 mm. Particles 30 having a size such that they are retained on a sieve having a nominal opening size of 22.6 mm may tend to have a melt time that is too long for a typical potpourri apparatus. Particles 30 having a size such that they pass a sieve having a nominal sieve opening size of 0.841 mm may be too small to conveniently handle. Particles 30 having a size within the aforesaid bounds may represent an appropriate balance between melting time and ease of particle 30 handling.

A plurality of particles 30 may collectively comprise a dose for dosing to a potpourri apparatus. A single dose of the particles 30 may comprise from about 1 g to about 27 g. A single dose of the particles 30 may comprise from about 5 g to about 27 g, alternatively from about 13 g to about 27 g, alternatively from about 14 g to about 20 g, alternatively from about 15 g to about 19 g, alternatively from about 18 g to about 19 g, alternatively combinations thereof and any whole numbers of grams or ranges of whole numbers of grams within any of the aforementioned ranges. The individual particles 30 forming the plurality of particles that can make up the dose can have a mass from about 0.95 mg to about 5 g. The plurality of particles 30 can be made up of particles 30 having different size, shape, and/or mass. The particles 30 in a dose can each have a maximum dimension less than about 15 mm. Each of the particles 30 in a dose can have a maximum dimension less than about 1 cm.

Figure 1:
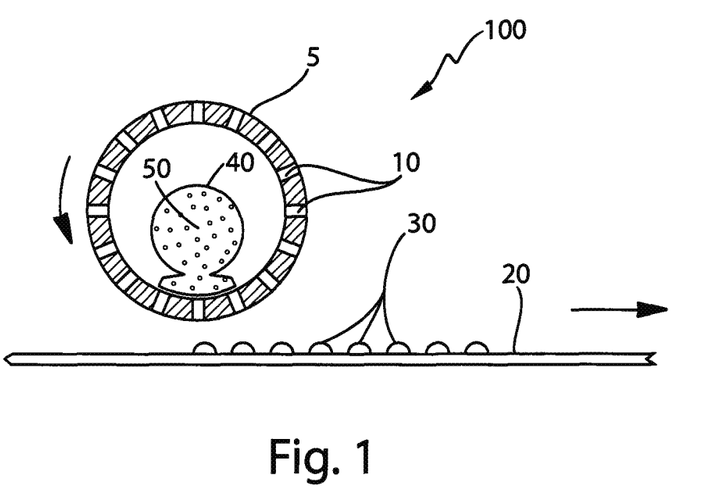
FIG. 1 is a schematic of a pastillation apparatus.

The particles 30 may be manufactured by a pastillation process. A schematic of a pastillation apparatus 100 is illustrated in FIG. 1. The steps of manufacturing according to such process can comprise providing the desired formulation as a viscous material 50. The viscous material 50 can comprise or consists of any of the formulations disclosed herein.

The viscous material 50 can comprise: more than about 40% by weight of the viscous material 50 of PEG (optionally about 40% to about 95% by weight of the viscous material 50 of PEG), wherein the PEG has a weight average molecular weight from about 5000 to about 11000; from about 0.1% to about 20% by weight of the viscous material 50 of perfume; and from about 0.1% to about 50% by weight of the viscous material 50 of starch granules, wherein said starch granules have a dextrose equivalent from 0 to about 40, wherein the starch granules have a grain size between about 1 µm to about 500 µm, and wherein the starch granules have a perfume load level of said perfume on the starch of less than about 10% by weight of the starch granules; wherein the viscous material 50 is formed into a plurality of particles 30, each of the particles 30 having a continuous phase of the PEG; wherein each of the particles 30 have a mass between about 0.95 mg to about 5 grams. The starch granules provided in manufacture can be substantially free from perfume. The viscous material 50 can be provided at a processing temperature less than about 20 degrees Celsius above the onset of solidification temperature as determined by differential scanning calorimetry.

Optional perfume microcapsules can be added as a slurry to the PEG and unencapsulated perfume to form the viscous material 50. Optionally, perfume microcapsules can be added as a powder to the PEG and unencapsulated perfume to form the viscous material 50. The viscous material 50 can be passed through small openings 10 and onto a moving conveyor surface 20 upon which the viscous material 50 is cooled below the glass transition temperature to form a plurality of particles 30. As illustrated in FIG. 1, the small openings 10 can be on a rotatable pastillation roll 5. Viscous material 50 can be distributed to the small openings 10 by a viscous material distributor 40. Particles can be formed on a ROTOFORMER, available from Sandvik Materials Technology, such as a Sandvik Rotoform 3000 having a 750 mm wide 10 m long belt. The cylinder of such rotoformer can have 2 mm diameter apertures set at 10 mm pitch in the cross machine direction and 9.35 mm in the machine direction. The cylinder of such rotoformer can be set 3 mm above the belt. The belt speed and rotational speed of the rotoformer can be 10 m/min. The melt can be fed to such rotoformer at 3.1 kg/min from a mixer and be at a temperature of about 50° C.

Each of the particles 30 can be substantially homogeneously structured. A substantially homogenously structured particle 30 is a particle in which the component materials forming the particle are substantially homogeneously mixed with one another. A substantially homogeneously structure particle 30 need not be perfectly homogeneous. There may be variations in the degree of homogeneity that is within limits of mixing processes used by those skilled in the art in commercial applications. Each of the particles 30 can have a continuous phase of the PEG. Each of the particles 30 can be a continuous phase of a mixture of the component materials forming the particle. So, for instance, if the particles comprise component materials A, B, and C, the particles 30 can be a continuous phase of a mixture A, B, and C. The same can be said for any number of component materials forming the particles 30, by way of nonlimiting example, three, four, five, or more component materials.

A homogeneously structured particle 30 is not a particle that has a core and coating, the particle being discrete from other particles having the same structure. A homogeneously structured particle 30 can be non-mechanically separable. That is, the component materials forming the homogeneously structured particle 30 may not be mechanically separated, for instance by a knife or fine pick. When the particles 30 are taken together as the composition, the composition can be substantially free from or even free from coated inclusions.

Homogeneously structured particles 30 can be substantially free or free from inclusions having a size greater than about 500 µm. Homogeneously structured particles 30 can be substantially free from or free from inclusions having a size greater than about 200 µm. Homogeneously structured particles 30 can be substantially free from or free from inclusions having a size greater than about 100 µm. Without being bound by theory, an abundance of large inclusions may be undesirable because they might interfere with the melting of the particle 30 in the potpourri apparatus or leave visually perceptible residue on the potpourri apparatus after use.

As used herein, size refers to the maximum dimension. A cross section of a homogeneously structured particle 30 does not reveal an overall structure of the particle to be a core and coating. M&M'S candy marketed by Mars, Incorporated, which is a chocolate core having a sugar coating, is not a homogeneously structured particle. In the case of M&M'S candy, the chocolate core and coating are mechanically separable. A chocolate covered raisin is similarly not a homogeneously structured particle. A homogeneously structured particle 30 is not a coated particle.

Figure 2:
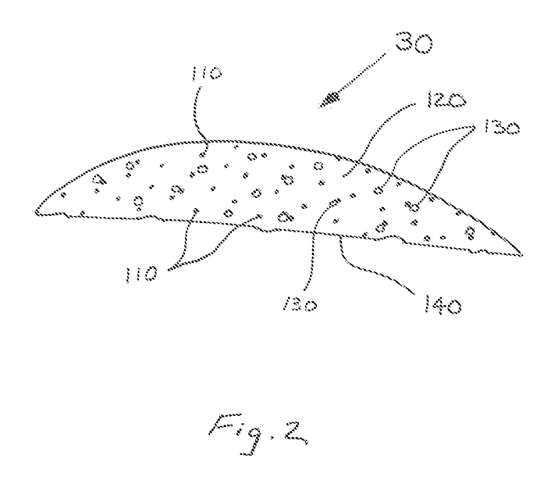
FIG. 2 is a schematic of a particle.

A schematic of a substantially homogeneous structured particle 30 is shown in FIG. 2. As shown in FIG. 2, the perfume 110 can be substantially randomly dispersed in the PEG 120. The perfume 110 can be unencapsulated perfume and or optionally perfume microcapsules. The starch granules 130 can be substantially randomly dispersed in the PEG 120 as well. As shown in FIG. 2, a substantially homogeneously structured particle 30 is not a particle having a core and coating arrangement. Rather, the constituent components of the formula are substantially homogeneously mixed with one another. Without being bound by theory, substantially homogeneous structured particles 30 are thought to possibly be less capital intense to produce and the processes to produce such particles 30 are thought to result in more uniform particles which are more acceptable to the consumer.

The particles 30 can have a substantially flat base 140. The particles 30 can have a flat base 140. The particles 30 can have a flat or substantially flat base 140. A flat base 140 or substantially flat base 140 can be beneficial because it can provide visual indicia of suitable processing conditions with respect to one or more of temperature of the melt, conveyor surface speed, conveyor surface temperature, or other process condition. When a melt from which particles 30 are prepared is at a sufficiently high temperature, the melt will tend to flow and a surface of the yet to be formed particle 30 will conform to the surface of the conveyor surface. If the temperature of the melt is too low, forming uniformly shaped particles 30 can be challenging.

The particles 30 can have a substantially circular flat base 140. The substantially circular flat base 140 can have a diameter between about 1 mm and about 12 mm. The substantially circular flat base 140 can have a diameter between about 2 mm and about 8 mm. The substantially circular flat base 140 can have a diameter between about 4 mm and about 6 mm.

Figure 3:
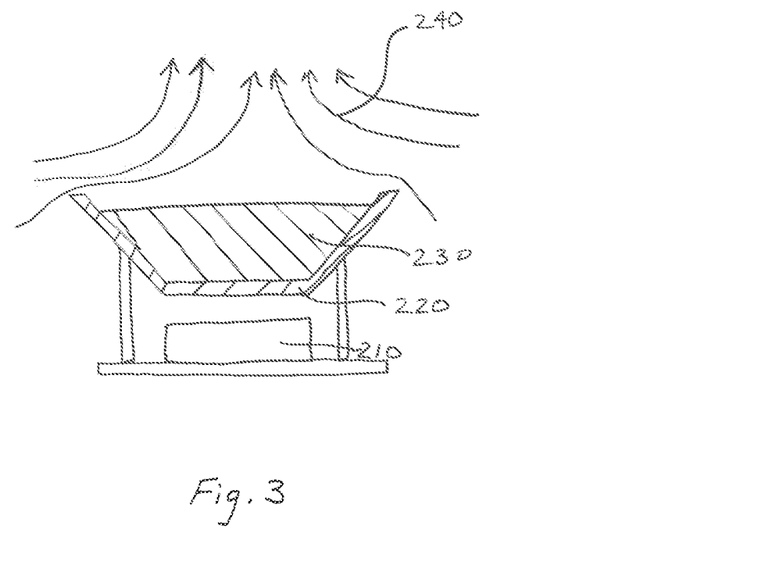
FIG. 3 is a schematic of a potpourri apparatus

The particles 30 can be employed in a process for imparting scent to air. A potpourri apparatus 200 is shown in FIG. 3. The potpourri apparatus 200 comprises a heater 210, a reservoir 220. The heater 210 can be flame. The heater 210 can be a resistive heating element that is powered by electricity. Heat from the heater 210 can be conducted or transferred from the heater 210 to the reservoir 220 through a solid, liquid, or gas conducting medium. Heat from the heater can be transferred from the heater 210 to the reservoir 220 by convection. The reservoir can be made of ceramic, metal, or other material capable of withstanding temperatures sufficiently high to melt the particles 30 disclosed herein. Together, the heater 210 and reservoir 220 can be housed in a housing. The housing can be provided with openings through which air 240 can be conducted or conveyed.

Particles 30 can be positioned in the reservoir 220 and melted to form a melt 230. Air 240 can be contacted with the melt 230. Volatile and semi-volatile perfume components dispersed in the wax can be transferred from the melt 230 to the air 240.

The process for imparting scent to air 240 can comprise the steps of: providing a plurality of particles 30 in a reservoir 220; heating the reservoir 220 to melt the particles 30 to form a melt 230; and contacting the melt 230 with air 240. The process for imparting scent to air 240 can further comprise a step of forceably moving the air 240 in proximity to said melt 240. The air 240 can be forcibly moved by a fan connected to a motor. Alternatively, air 240 can be moved in proximity to the melt 240 by convection as air 240 is heated when overlying the melt 240 and rises away from melt 240. Providing for air moving in proximity to the melt 240 can provide for an increase in the mass of perfume released.

The potpourri apparatus 200 can be an EVERYDAY CERAMIC TARTS WAX POTPOURRI WARMER Item #1228663 sold by Yankee Candle Company, South Deerfield, Mass., United States of America. The potpourri apparatus 200 can be an AMBER MOSAIC TARTS WAX POTPOURRI WARMER Item #1226799 sold by Yankee Candle Company, South Deerfield, Mass., United States of America.

The reservoir can have a volume less than about 300 mL. The reservoir can have a volume less than about 300 mL. The reservoir can have a volume less than about 100 mL. The reservoir can have a volume less than about 50 mL. The reservoir can have a volume less than about 30 mL. Smaller volumes are thought to be more convenient to use by the user and reduce the potential for scent habituation which can diminish the perceived benefit from operating the process. Larger volumes are associated with a longer operation duration for the potpourri apparatus 200.

The potpourri apparatus 200 can operated for a period of time during which the melt 230 releases perfume at the level desired by the user. Once the perfume is spent as such, the user can turn off the heater 210 or blow out the heater 210 and the melt will solidify in the reservoir 220. The user can then remove the solidified material from the reservoir 220 and place fresh particles 30 in the reservoir for subsequent use of the potpourri apparatus 200. Alternatively, the user can remove the reservoir 220 from the potpourri apparatus 200 when the melt 230 is still sufficiently warm to be in a melted condition and pour the contents of the reservoir 220 into a suitable waste container.

The process for imparting scent to air can be as follows with the numbers in bracket corresponding to how the process may be described and claimed: [1] A process for imparting scent to air comprising the steps of: providing a plurality of particles (30) in a reservoir (220); heating said reservoir to melt said particles to form a melt (230); and contacting said melt with air (240); wherein said particles comprise: 40% to 95% by weight of said particles of polyethylene glycol (120), wherein said polyethylene glycol has a weight average molecular weight from 5000 to 11000; 0.1% to 20% by weight of said particles of perfume (110); and 0.1% to 50% by weight of said particles of starch granules (130), wherein said starch granules have a dextrose equivalent from 0 to 40, wherein said starch granules have a grain size of from 1 μm to 500 μm, and wherein said starch granules have a starch perfume load level of said perfume on said starch granules of from 0% to 10% by weight of the starch granules; wherein said particles are substantially homogenously structured particles; and wherein each of said particles has a mass between 0.95 mg to 5 grams. [2] The composition according to [1], wherein said particles are substantially free from inclusions having a size greater than 500 μm. [3] The composition according to [1] or [2], wherein said starch granules have a dextrose equivalent from 0 to 25. [4] The composition according to any one of [1] through [3], wherein said starch granules have a grain size of from 1 μm to 200 μm. [5] The composition according to any one of [1] through [4], wherein said polyethylene glycol has a polyethylene glycol perfume load level of said perfume on said polyethylene glycol, wherein said polyethylene glycol perfume load level is greater than said starch perfume load level. [6] The composition according to any one of [1] through [5], wherein said particles further comprise dye. [7] The composition according to any one of [1] through [6], wherein said perfume comprises encapsulated perfume. [8] The composition according to any one of [1] through [7], wherein said perfume comprises unencapsulated perfume. [9] The composition according to any one of [1] through [8], wherein said starch granules are unmodified starch. [10] The composition according to any one of [1] through [9], wherein said particles are substantially free from inclusions having a size greater than 200 μm. [11] The composition according to any one of [1] through [10], wherein said particles are substantially free from inclusions having a size greater than 100 μm. [12] The composition according to any one of [1] through [11], wherein said starch granules have a grain size of from 1 μm to 30 μm. [13] The composition according to any one of [1] through [12], wherein said particles have a flat or substantially flat base. [14] The composition according to any one of [1] through [13], wherein said particles are in a dose of from 1 g to 27 g. [15] The composition according to any one of [1] through [14], wherein said particles are retained on an ASTM E11-13 number 20 sieve.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A process for imparting scent to air comprising the steps of:
   providing a plurality of particles in a reservoir;
   heating said reservoir to melt said particles to form a melt; and
   contacting said melt with air;
   wherein said particles comprise:
   about 40% to about 95% by weight polyethylene glycol, wherein said polyethylene glycol has a weight average molecular weight from about 5000 to about 11000;
   about 0.1% to about 20% by weight perfume; and
   about 0.1% to about 50% by weight starch granules, wherein said starch granules have a dextrose equivalent from 0 to about 40, wherein said starch granules have a grain size of from about 1 µm to about 500 µm, and wherein said starch granules have a starch perfume load level of said perfume on said starch granules of from 0% to about 10% by weight of said starch granules;
   wherein said particles are substantially homogenously structured particles; and
   wherein each of said particles has a mass between about 0.95 mg to about 5 grams.

2. The process according to claim 1, where the step of heating said reservoir is performed with a flame or resistive heating element.

3. The process according to claim 1, wherein said process further comprises a step of forceably moving said air in proximity to said melt.

4. The process according to claim 1, wherein said particles are substantially free from inclusions having a size greater than about 200 µm.

5. The process according to claim 1, wherein said starch granules have a dextrose equivalent from 0 to about 25.

6. The process according to claim 1, wherein said starch granules are unmodified starch.

7. The process according to claim 1, wherein said starch granules have a grain size of from about 1 µm to about 200 µm.

8. The process according to claim 1, wherein said starch granules have a grain size of from about 1 µm to about 30 µm.

9. The process according to claim 1, wherein said polyethylene glycol has a polyethylene glycol perfume load level of said perfume on said polyethylene glycol, wherein said polyethylene glycol perfume load level is greater than said starch perfume load level.

10. The process according to claim 1, wherein said particles have a flat or substantially flat base.

11. The process according to claim 1, wherein said perfume comprises unencapsulated perfume.

12. The process according to claim 1, wherein said particles are substantially free from particulate inclusions having a size greater than about 500 µm.

13. The process according to claim 12, wherein said starch granules have a dextrose equivalent from 0 to about 25.

14. The process according to claim 13, wherein said starch granules have a grain size of from about 1 µm to about 200 µm.

15. The process according to claim 14, wherein said particles further comprise dye.

16. The process according to claim 15, wherein said polyethylene glycol has a polyethylene glycol perfume load level of said perfume on said polyethylene glycol, wherein said polyethylene glycol perfume load level is greater than said starch perfume load level.

17. The process according to claim 16, wherein said particles have a flat or substantially flat base.

18. The process according to claim 17, wherein said perfume comprises unencapsulated perfume.

19. A composition comprising a plurality of particles, wherein said particles comprise:
   about 40% to about 80% by weight polyethylene glycol, wherein said polyethylene glycol has a weight average molecular weight from about 5000 to about 11000;
   about 0.1% to about 20% by weight perfume; and
   about 0.1% to about 50% by weight starch granules, wherein said starch granules have a dextrose equivalent from 0 to about 40, wherein said starch granules have a grain size of from about 1 µm to about 200 µm, and wherein said starch granules have a starch perfume load level of said perfume on said starch granules of from 0% to about 10% by weight of said starch granules;
   wherein said particles are substantially homogenously structured particles;
   wherein each of said particles has a mass between about 0.95 mg to about 5 grams;
   wherein said particles are substantially free from particulate inclusions having a size greater than about 500 µm;
   wherein said starch granules have a dextrose equivalent from 0 to about 25;
   wherein said polyethylene glycol has a polyethylene glycol perfume load level of said perfume on said polyethylene glycol, wherein said polyethylene glycol perfume load level is greater than said starch perfume load level;
   wherein said perfume comprises unencapsulated perfume;
   wherein said particles are retained on an ASTM E11-13 number 20 sieve.

* * * * *